(12) United States Patent
Wang et al.

(10) Patent No.: US 10,881,761 B2
(45) Date of Patent: Jan. 5, 2021

(54) PREPARATION OF HIGH PURITY COLLAGEN PARTICLES AND USES THEREOF

(71) Applicant: Acro Biomedical Company. Ltd., Kaohsiung (TW)

(72) Inventors: Jun-Jie Wang, Tainan (TW); Pei-Hua Tsai, Tainan (TW); Kai-Chi Ku, Pingtung County (TW); Dar-Jen Hsieh, Kaohsiung (TW)

(73) Assignee: ACRO BIOMEDICAL COMPANY. LTD., Kaohsiung (TW)

( * ) Notice: Subject to any disclaimer, the term of this patent is extended or adjusted under 35 U.S.C. 154(b) by 305 days.

(21) Appl. No.: 15/739,163

(22) PCT Filed: Aug. 11, 2016

(86) PCT No.: PCT/CN2016/094634
§ 371 (c)(1),
(2) Date: Dec. 22, 2017

(87) PCT Pub. No.: WO2017/025054
PCT Pub. Date: Feb. 16, 2017

(65) Prior Publication Data
US 2020/0040030 A1 Feb. 6, 2020

Related U.S. Application Data

(60) Provisional application No. 62/203,904, filed on Aug. 11, 2015.

(51) Int. Cl.
| | |
|---|---|
| *C07K 1/36* | (2006.01) |
| *A61L 27/24* | (2006.01) |
| *A61K 8/65* | (2006.01) |
| *A61L 27/36* | (2006.01) |
| *C07K 14/78* | (2006.01) |
| *A61L 27/20* | (2006.01) |
| *A61L 27/52* | (2006.01) |
| *A61K 38/00* | (2006.01) |

(52) U.S. Cl.
CPC ........... *A61L 27/3612* (2013.01); *A61L 27/20* (2013.01); *A61L 27/24* (2013.01); *A61L 27/362* (2013.01); *A61L 27/3654* (2013.01); *A61L 27/3687* (2013.01); *A61L 27/3691* (2013.01); *A61L 27/52* (2013.01); *C07K 1/36* (2013.01); *C07K 14/78* (2013.01); *A61L 2400/06* (2013.01); *A61L 2400/12* (2013.01); *A61L 2430/06* (2013.01); *A61L 2430/34* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 2008/0077251 A1 | 3/2008 | Chen et al. | |
| 2010/0209943 A1* | 8/2010 | Goldberg | C12Q 1/37 435/7.4 |
| 2015/0037436 A1 | 2/2015 | Huang et al. | |
| 2015/0328561 A1* | 11/2015 | Ginosar | B01D 11/0488 210/634 |
| 2016/0051731 A1 | 2/2016 | Matsuda et al. | |

FOREIGN PATENT DOCUMENTS

| | | | | |
|---|---|---|---|---|
| EP | 2578247 A2 * | 4/2013 | ......... | A61L 27/3683 |
| WO | 2011042794 | 4/2011 | | |
| WO | 2012166538 | 12/2012 | | |

OTHER PUBLICATIONS

Crapo et al. (2011) An Overview of Tissue and Whole Organ Decellularization Processes, Biomaterials, vol. 32, No. 12, pp. 3233-3243.*
Casali D.M. (2014) Processing Tissue Engineering Matrix Materials with Supercritical CO2, Annual meeting, Atlanta, GA. pp. 1-3.*

* cited by examiner

*Primary Examiner* — Manjunath N Rao
*Assistant Examiner* — Samuel W Liu

(57) ABSTRACT

Disclosed herein is a method of producing collagen particles. Each of the collagen particle is characterized in having a particle size of about 10-250 μm, in which the integrity of collagen fibers therein is relatively intact.

13 Claims, 2 Drawing Sheets

(A)

(B)

(A)

(B)

PREPARATION OF HIGH PURITY COLLAGEN PARTICLES AND USES THEREOF

CROSS-REFERENCE TO RELATED APPLICATIONS

This application is a U.S. National Stage Filing under 35 U.S.C. 371 from International Patent Application Serial No. PCT/CN2016/094634, filed Aug. 11, 2016, and published on Feb. 16, 2017, which claims the priority of U.S. Serial No. 62/203,904, filed Aug. 11, 2015, the disclosure of which are incorporated by reference herein in their entireties.

BACKGROUND OF THE INVENTION

1. Field of the Invention

The present disclosure in general relates to the field of methods for producing collagens, particularly, improved methods for producing collagen particles suitable for use as biological scaffolds for cells to grow thereon, such as dermal fillers for injections during a plastic surgery (e.g., a cosmetic surgery) for soft tissue augmentation (e.g., smoothing facial lines and wrinkles); or as wound dressings for promoting wound healing.

2. Description of Related Art

Collagen is an insoluble fibrous protein that occurs in vertebrates as the chief constituent of the fibrils of connective tissue such as skin. The conventional process of obtaining collagen is time consuming and inefficient, and oftentimes destroys the integrity of the collagens, rendering them unsuitable as a biological scaffold if they were intended to be used as an implant in the cosmetic surgery or in wound healing. Further, most commercially available collagens such as those sold under the name Zyderm, and Zyplast are harvested from cow skin, which cannot be used in all patients due to severe allergic reactions they have on a significant population of hosts, especially those with a history of autoimmune diseases. In addition, bovine collagen does not exhibit long-term residence at the injection site, and thus requires periodic touch-up injections. It is believed that the short residence of the bovine collagen is due to the integrity of the collagen being destroyed when it was extracted from the cow hides, thereby resulting the collagen being easily absorbed by the host.

Collagen that are of human origins such as Cosmoderm, and Cosmoplast have been developed, however, they are very expensive due to the limited sources (i.e., human foreskins of circumcisions). Alternatively, patients may use collagen derived from his/her own adipose tissue extracted by liposuction procedures and processed into injectable form for immediate use or stored for future use. However, they too, suffer from the same defect as that of bovine collagen, in that the integrity of the collagen is destroyed during isolation procedures.

Accordingly, there exist in the related art a need of an improved process for producing collagen, in which the native structure and conformation of collagen are preserved during the isolation procedures, so that the thus produced collage product may serve as a three-dimensional scaffold for host cells to grow thereon without eliciting significant immune response.

SUMMARY

The present disclosure was created by the present inventors to overcome the above-noted problems in the production of collagen particles, especially in the production of collagen particles characterized in having the native conformation of collagens from the skin of an animal (e.g., the skin of a hog or a cow).

Accordingly, it is the first aspect of this disclosure to provide a method for preparing collagen particles. The method comprises steps of,
(1) subjecting an animal skin having a thickness of about 0.1-1 mm to a decellularization process;
(2) subjecting the decellularized animal skin of step (1) to the treatment of an aqueous solution comprising a non-ionic surfactant;
(3) subjecting the aqueous solution treated animal skin of the step (2) to the treatment of a protease;
(4) subjecting the protease treated animal skin of step (3) to the treatment of a nuclease;
(5) subjecting the nuclease treated animal skin of step (4) to a de-ionization process;
(6) subjecting the de-ionized animal skin of step (5) to a chemical removal process so as to produce a collagen matrix; and
(7) subjecting the collagen matrix of step (6) to a granulation process so as to produce the collagen particle having a size of about 10-250 μm.

According to some embodiments, in the step (1), the animal skin having a thickness of about 0.1-1 mm is subject to the treatment of a supercritical fluid (SCF) under a pressure of about 100-500 bar at a temperature between 30-50° C. for about 20 min to 5 days.

The SCF may be any of a supercritical carbon dioxide ($scCO_2$), a supercritical nitrous oxide ($scN_2O$), a supercritical water ($scH_2O$), a supercritical alkane, a supercritical alkene, a supercritical alcohol or a supercritical acetone. In one example, the SCF is $scCO_2$. In another example, the SCF is $scN_2O$.

According to one preferred embodiment, the decellularization process is carried out at a condition, in which the temperature is about 37° C., and the pressure is about 350 Bar, for 20 min.

According to some embodiments, in the step (2), the decellularized animal skin of step (1) is treated with an aqueous solution containing a surfactant selected from the group consisting of, octylphenol ethoxylates (e.g., Triton X series), sorbitan monostearate, polysorbate, poloxomer, nonoxynols, cetyl alcohol, and alkylpolyglucoside. Optionally, the aqueous solution may further comprise an anionic surfactant, such as lauryl sulfonic acid, dodecyl sulfonic acid, sodium dodecyl sulfate (SDS), dodecyl benzene sulfonic acid, tridecyl benzene sulfonic acid, alkyl-phenoxy benzene disulfonic acid, naphthalene sulfonic acid, alkyl-naphthalene sulfonic acid, and alkenyl-naphthalene. Still optionally, the aqueous solution may further comprise a salt, such as sodium chloride, potassium chloride, and the like. In one preferred example, the anionic surfactant is sodium dodecyl sulfate (SDS).

According to some embodiments, the protease of the step (3) may be selected from the group consisting of, pepsin, trypsin, chymotrypsin, papain, chymopapain, bromelain, actinidain, proteinase A, proteinase K, peptidase, ficin, calpain, caspase, and a combination thereof.

According to some embodiments, in the step (4), the protease treated animal skin of step (3) is treated with a nuclease that is a DNA nuclease or a RNA nuclease.

Optionally, the product of step (4) may be further treated with the aqueous solution of step (2), which comprises a non-ionic surfactant selected from the group consisting of, octylphenol ethoxylates (e.g., Triton X series), sorbitan monostearate, polysorbate, poloxomer, nonoxynols, cetyl alcohol, and alkylpolyglucoside. In one preferred example, the aqueous solution comprises 1% Triton X-100. Still optionally, the aqueous solution may further comprise an anionic surfactant, such as lauryl sulfonic acid, dodecyl sulfonic acid, dodecyl benzene sulfonic acid, tridecyl benzene sulfonic acid, alkyl-phenoxy benzene disulfonic acid, naphthalene sulfonic acid, alkyl-naphthalene sulfonic acid, and alkenyl-naphthalene. Still optionally, the aqueous solution may further comprise a salt, such as sodium chloride, potassium chloride, and the like. In one preferred example, the anionic surfactant is sodium dodecyl sulfate (SDS).

According to some embodiments, in the step (5), the nuclease treated animal skin of step (4) is treated with a hydrogen peroxide solution for an hour.

According to some embodiments, in the step (6), the chemical removal process includes subjecting the de-ionized product of the step (5) to the treatment of a supercritical fluid under a pressure of about 100-500 bar at a temperature between 30-50° C. for about 20 min to 5 days.

The supercritical fluid may be any of a supercritical carbon dioxide ($scCO_2$), a supercritical nitrous oxide ($scN_2O$), a supercritical water ($scH_2O$), a supercritical alkane, a supercritical alkene, a supercritical alcohol or a supercritical acetone. In one example, the SCF is $scCO_2$. In another example, the SCF is $scN_2O$.

According to preferred embodiments, the chemical removal process is carried out in the presence of a co-solvent at a condition, in which the temperature is about 37° C., and the pressure is about 350 Bar, for about 60 min. In one example, the co-solvent is ethanol, which is applied with SCF in a volume ratio of 1:10.

According to further embodiments, in the step (7), the granulation process is performed by cutting or grinding the collagen matrix of step (6) and thereby producing the collagen particle having a particle size of about 10-250 μm. The thus produced collagen particle is constituted by collagens, in which their native structures and conformations are preserved, so that they may serve as a three-dimensional bio-scaffold that allows cells to grow therein after being applied onto a subject.

It is therefore the second aspect of the present disclosure to provide a method of treating a skin condition of a subject, in which the skin conditions are wounds, lines and/or depression on the skin. The method comprises the step of, administering a sufficient amount of the collagen particles produced by the present method under the skin of the subject, so as ameliorating or improving the skin condition. The skin condition may be wounds, lines and/or depression on the skin. Examples of wounds include, but are not limited to, surgical wounds (such as incisions), ulcers, and any other injury to the body in which the skin or other tissue is broken, cut, pierced, or torn. Examples of lines and/or depressions on the skin (e.g., facial skin) include, but are not limited to, frown lines, lines around the mouth, worry lines, crows feet, smile lines, and facial scarring from acne or injury. In one preferred embodiment, the collagen particles are used as dermal fillers to augment soft tissue of a subject, and are administered to the subject by injection with a needle, such as a needle of 32 gauge or less. In other embodiments, the collagen particles are used as wound dressings, and are administered to the subject by an applicator that spreads the collagen particles evenly on top of the wounds.

It is therefore the third aspect of the present disclosure to provide a kit for treating a skin condition described above during a cosmetic surgery. The components included in the kits are: a container, the collagen particles produced by the present method, which are characterized in that the integrity of collagen fibers in the collagen particles are relatively intact and each particles is about 10-250 μm in diameter; and a legend associated with the container to direct a user how to use the collagen particles of the present disclosure. The legend may be in a form of pamphlet, tape, CD, VCD or DVD.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF THE PREFERRED EMBODIMENTS

Figure 1:
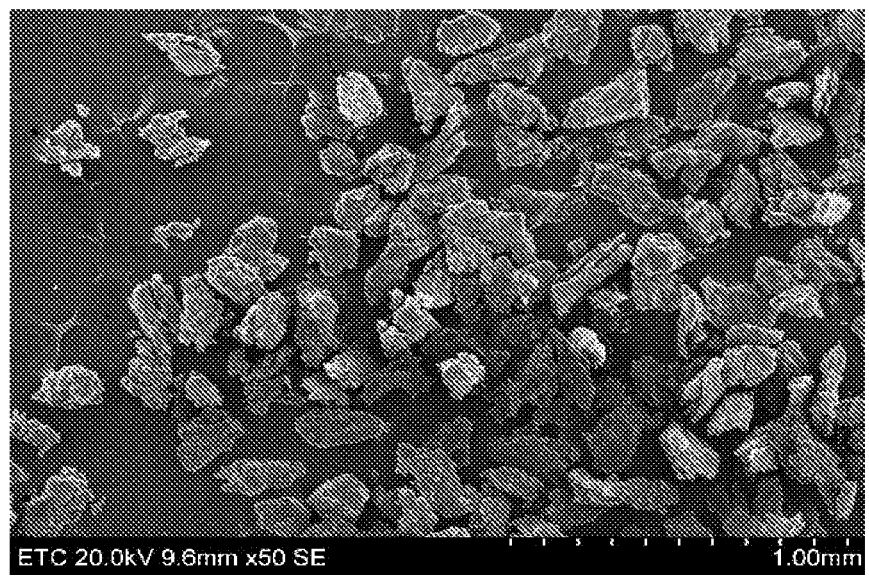
FIG. 1 is an electromicroscope (EM) photograph of the present collagen particle respectively taken at a magnification of (A) 50×, and (B) 20,000×, in accordance with one embodiment of the present disclosure.
Figure 1:
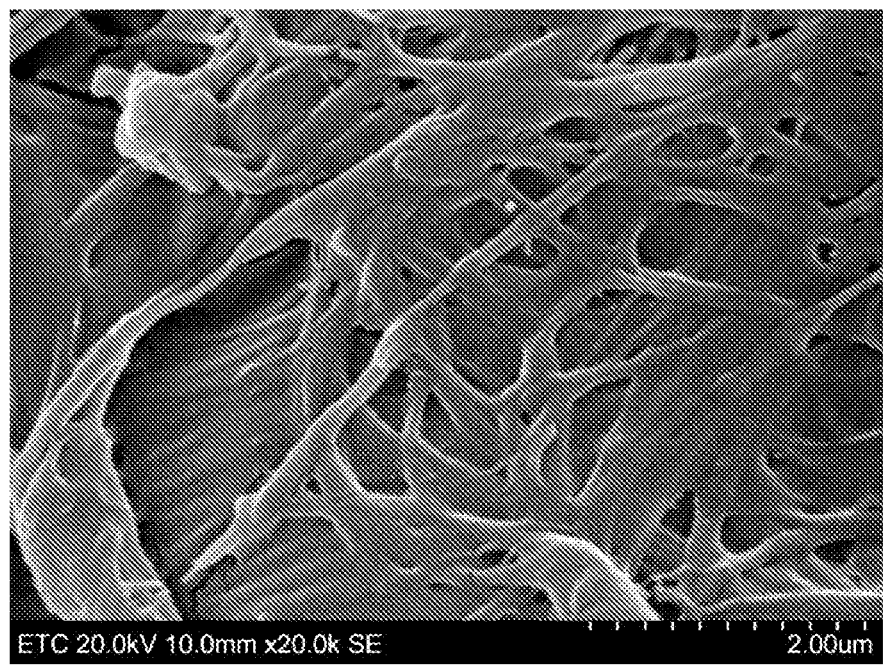

The detailed description provided below in connection with the appended drawings is intended as a description of the present disclosure and is not intended to represent the only forms in which the present disclosure may be constructed or utilized.

The singular forms "a", "and", and "the" are used herein to include plural referents unless the context clearly dictates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The present disclosure pertains, among others, a novel method of producing a collagen particle, the novel collagen particle produced by the method, and a novel use of the thus produced collagen particle.

The first aspect of the present disclosure involves a novel method of producing a collagen particle, in which the native structure and conformation of collagen is preserved, thus may provide an optimal micro-environment for host tissue cells to grow thereon once the present collagen particle is injected into the host.

Accordingly, the present method includes at least, the following steps,
(1) subjecting an animal skin having a thickness of about 0.1-1 mm to a decellularization process;
(2) subjecting the decellularized animal skin of step (1) to the treatment of an aqueous solution comprising a non-ionic surfactant;
(3) subjecting the aqueous solution treated animal skin of the step (2) to the treatment of a protease;
(4) subjecting the protease treated animal skin of step (3) to the treatment of a nuclease;
(5) subjecting the nuclease treated animal skin of step (4) to a de-ionization process;
(6) subjecting the de-ionized animal skin of step (5) to a chemical removal process so as to produce a collagen matrix; and
(7) subjecting the collagen matrix of step (6) to a granulation process so as to produce the collagen particle having a size of about 10-250 μm.

Before starting the present method, the animal skin, preferably obtained by skinning an animal, is washed, de-haired, and de-fatted. Preferably, animals suitable for use in the present disclosure are farm animals, which include but are not limited to, pigs, cattle, cows, bulls, sheep, goats, donkeys, rabbits, ducks, geese, and fowls. The de-haired and de-fatted process may be carried out by any mechanical or chemical method known in the related art. For example, the hairs may be removed by treating the animal skin (e.g., a porcine rind) with an acid, whereas the fat may be removed by treating the animal skin with an enzyme (e.g., a lipase) or a chemical (e.g., a detergent), alternatively, by mechanically cutting it off.

Next, the surface layer of the de-haired and de-fatted animal skin is removed by a dermatome, so that an animal skin having a thickness of about 0.1 to 1 mm is produced, such as an animal skin having a thickness of about 0.1, 0.2, 0.3, 0.4, 0.5, 0.6, 0.7, 0.8, 0.9 and 1.0 mm; more preferably, about 0.2 to 0.6 mm, such as 0.2, 0.3, 0.4, 0.5 and 0.6 mm; most preferably, about 0.3 mm. The thus produced animal skin is then used in the present method.

Optionally, the afore-produced animal skin, which has a thickness between 0.1 to 1 mm, is treated with an alkaline agent at a temperature between 0-55° C. for about 0.1-24 hours to remove any residual hair and/or fat. Examples of alkaline agent suitable for used in the present method include, but are not limited to, sodium hydroxide, potassium hydroxide, calcium hydroxide, urea, sodium sulfide, calcium thioacetate and etc. Preferably, the animal skin is a porcine rind having a thickness of about 0.1-0.6 mm, and is treated with a sodium hydroxide solution about 0.1-1 N at 4° C. for about 1 hour.

In the step (1), the animal skin having a thickness between 0.1-1 mm is subjected to a decellularization process. The decellularization process is performed for the purpose of removing the cellular materials from the animal skin, while preserving the physical and biochemical properties of collagen, so that it may better serve as a tissue scaffold. Accordingly, in step (1), the animal skin having a thickness between 0.1-1 mm is subject to the treatment of a supercritical fluid (SCF) under a pressure of about 100-500 bar, such as 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 and 500 bar; preferably about 150-450 bar, such as 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, and 450 Bar; and more preferably about 200-400 Bar, such as 200, 210, 220, 230, 240, 250, 260, 270, 280, 290, 300, 310, 320, 330, 340, 350, 360, 370, 380, 390, and 400 Bar. Further, the step (1) is performed at a temperature between 30-50° C., such as 30, 31, 32, 34, 35, 36, 37, 38, 39, 40, 41, 42, 43, 44, 45, 46, 47, 48, 49 and 50° C.; preferably between 35-45° C., such as 35, 36, 37, 38, 39, 40, 41, 42, 43, 44, and 45° C.; for about 20 min to 5 days, such as 20, 30, 40, 50, and 60 mins; 2, 3, 4, 5, 6, 7, 8, 9, 10, 11, 12, 13, 14, 15, 16, 17, 18, 19, 20, 21, 22, 23, and 24 hrs; 2, 3, 4, and 5 days. In some examples, the animal skin having a thickness between 0.1 to 1 mm is treated with SCF for about 1 to 24 hrs. In other examples, the animal skin having a thickness between 0.1 to 1 mm is treated with SCF for about 2 to 5 days.

The SCF may be any of a supercritical carbon dioxide ($scCO_2$), a supercritical nitrous oxide ($scN_2O$), a supercritical water ($scH_2O$), a supercritical alkane, a supercritical alkene, a supercritical alcohol or a supercritical acetone. In one example, the SCF is $scCO_2$, for $scCO_2$ has mild critical condition of 37° C. at about 350 Bar, hence allows biological materials to be removed at or near body temperature (i.e., 37° C.). In another preferred example, the SCF is $scN_2O$.

In subsequent step (2), the decellularized animal skin of step (1) is washed with an aqueous solution containing a non-ionic surfactant, so as to remove any residual cellular matters. Examples of suitable non-ionic surfactant that may be used in the aqueous solution include, but are not limited to, octylphenol ethoxylates (e.g., Triton X series), sorbitan monostearate, polysorbate, poloxomer, nonoxynols, cetyl alcohol, alkylpolyglucoside, and etc. Preferably, the non-ionic surfactant is octylphenol ethoxylates, i.e., the Triton X series, which include but are not limited to, Triton X-15, Triton X-35, Triton X-45, Triton X-100, Triton X-102, Triton X-114, and etc. According to some embodiments of the present disclosure, the non-ionic surfactant is Triton X-100, and is present in the aqueous solution in a concentration between about 0.1-10% (wt %), such as 0.1, 0.2, 0.3, 0.4, 0.5, 0.6, 0.7, 0.8, 0.9, 1, 2, 3, 4, 5, 6, 7, 8, 9, or 10% (wt %). Preferably, the non-ionic surfactant is present in the aqueous solution in a concentration between about 0.5-5% (wt %), such as 0.5, 0.6, 0.7, 0.8, 0.9, 1, 2, 3, 4 or 5% (wt %). According to one preferred embodiment, the aqueous solution contains about 1% (wt) Triton X-100.

Optionally, the aqueous solution may further comprise an anionic surfactant, such as lauryl sulfonic acid, dodecyl sulfonic acid, dodecyl benzene sulfonic acid, tridecyl benzene sulfonic acid, alkyl-phenoxy benzene disulfonic acid, naphthalene sulfonic acid, alkyl-naphthalene sulfonic acid, and alkenyl-naphthalene, Still optionally, the aqueous solution may further comprise a salt, such as sodium chloride, potassium chloride, and the like. In one preferred example, the anionic surfactant is sodium dodecyl sulfate (SDS).

Next, in step (3), the aqueous solution washed animal skin of step (2) is enzymatically digested with a protease. The enzymatic digestion treatment in the present step is mild so as to preserve the native structure and conformation of collagen fiber. Examples of suitable protease that may be used in step (4) include, but are not limited to, pepsin, trypsin, chymotrypsin, papain, chymopapain, bromelain, actinidain, proteinase A, proteinase K, peptidase, ficin, calpain, caspase, or a combination thereof. In one example, the protease is pepsin. In another example, the protease is a mixture of trypsin and chemotrypsin. Preferably, the protease is present in a concentration of about 0.001-0.1% (wt %), such as 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, and 0.1% (wt %); more preferably, about 0.002-0.05% (wt), such as 0.002, 0.003, 0.004, 0.005, 0.006, 0.007, 0.008, 0.009, 0.01, 0.02, 0.03, 0.04, and 0.05% (wt %). According to one preferred embodiment, the aqueous solution washed animal skin of step (2) is digested with about 0.05% (wt %) pepsin for about 8-24 hrs, such as 8, 9, 10, 11, 12, 13, 14, 15, 16, 17, 18, 19, 20, 21, 22, 23 and 24 hrs; preferably for about 12 to 20 hrs, such as 12, 13, 14, 15, 16, 17, 18, 19, and 20 hrs.

In step (4), the product of step (3) is treated with a nuclease, which may be a DNA nuclease or a RNA nuclease, preferably a non-specific DNA/RNA nuclease. According to some embodiments of the present disclosure, the produced in step (3) is treated with a nuclease at 37° C. for about 1 hr.

Optionally, the product of step (4) may be further treated with a glycoside hydrolase, such as alpha-galactosidase, so as to remove any residual galactosyl moiety from the nuclease treated product of the step (3).

Still optionally, the product of step (4) may be further treated with the aqueous solution as described above, so as to remove any residual cellular matters. Preferably, the aqueous solution contains 1% Triton X-100, and may further contain an anionic surfactant, such as SDS.

In subsequent step (5), the product of step (4) is subject to the treatment of a de-ionization process, which comprises treating the nuclease treated animal skin of step (4) with a hydrogen peroxide solution for about 0.5-5 hrs, such as about 0.5, 1, 1.5, 2, 2.5, 3.0, 3.5, 4.0, 4.5 and 5 hrs. Preferably, the hydrogen peroxide is present in the solution at a concentration from about 0.1-3% (wt %), such as about 0.1, 0.2, 0.3, 0.4, 0.5, 0.6, 0.7, 0.8, 0.9, 1, 1.5, 2, 2.5 or 3% (wt %). According to one preferred embodiment, the product of step (4) is treated with 1% hydrogen peroxide solution for about 1 hr.

Next, in step (6), the product of the step (5) is subject to a chemical removal process, which comprises treating the de-ionized product of the step (5) with a supercritical fluid. Similar to the condition as described animal skin in step (2), the same or different supercritical fluid may be used in the present step, under a pressure of about 100-500 bar at a temperature between 30-50° C. for about 20 min to 5 days. In one example, the SCF is scCO$_2$. In another example, the SCF is scN$_2$O. According to one preferred embodiment, the SCF is applied is applied to the product of step (5) along with a co-solvent, and the chemical removal process is performed at a condition, in which the temperature is about 37° C., and the pressure is about 350 Bar, for about 60 min. The co-solvent may be a C$_{1-4}$ alcohol, which includes but is not limited to, ethanol, propanol, isopropanol, butanol, isobutanol, sec-butanol, t-butanol, and cyclobutanol. In some preferred examples, the co-solvent is ethanol, and is applied with the SCF in a volume ration from 1:20 to 1:4, such as 1:20, 1:19, 1:18, 1:17, 1:16, 1:15, 1:14, 1:13, 1:10, 1:9, 1:8, 1:7, 1:6, 1:5, and 1:4. In one preferred embodiment, the ethanol is applied with SCF in a volume ration of 1:19.

In another embodiment, the ethanol is applied with SCF in the volume ratio of 1:10. In still another embodiment, the ethanol is applied with SCF in the volume ratio of 1:4.

In the final step (7), the product of the step (6) is granulated so as to produce the desired collagen particle suitable for administering via injection. The granulation process is performed by cutting, grinding or shearing the product of step (6) (i.e., a collagen matrix) in the presence of liquid nitrogen so as to produce the collagen particle having a particle size of about 10-250 µm, such as about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 170, 175, 180, 185, 190, 195, 200, 205, 210, 220, 225, 230, 235, 240, 245, and 250 µm. In one preferred embodiment, the collagen particle has a size about 50-100 µm, such as about 50, 55, 60, 65, 70, 75, 80, 85, 90, 95, and 100 µm. In another embodiment, the collagen particle has a size about 100-150 µm, such as about 100, 105, 110, 115, 120, 125, 130, 135, 140, 145, and 150 µm. In still another embodiment, the collagen particle has a size about 150-250 µm, such as about 150, 155, 160, 170, 175, 180, 185, 190, 195, 200, 205, 210, 220, 225, 230, 235, 240, 245, and 250 µm. The thus produced collagen particle is characterized in having collagen fibers, in which the native structures and conformations of the collagen fibers are preserved, so that the collagen particle of the present disclosure may serve as a bio-scaffold that allows cells to grow thereon.

The thus produced collagen particle may be used as dermal fillers and are administered to a desirable site of a subject (e.g., the face) by use of a needle of 32 gauge or less, such as 32, 30, 29, 28, 27, 26 s, 26, 25, 24, 23, 22 s, 22, 21, 20, 19, 18, 17, 16, 15, 14, 13, 12, 11, 10, 9, 8, or 7 gauge. In one example, the present collagen particle was injected by a needle of 30 gauge. In another example, the present collagen particle was injected by a needle of 27 gauge.

Alternatively, the thus produced collagen particles may be used as wound dressings and are administered to the wound of a subject, by use of an applicator, that sprays the present collagen solution evenly on top of wounds, which include but are not limited to, surgical wounds (such as an incisions), ulcers, and any other injury to the body hi which the skin or other tissue is broken, cut, pierced, or torn; lines and/or depression on the facial skin that include, but are not limited to, frown lines, lines around the mouth, worry lines, crows feet, smile lines, and facial scarring from acne or injury.

The present method differs from the prior art method in that, it does not require the use of a cross-linking agent or the addition of a salt to stabilize the collagen matrix during the preparation, nor does it require extracting collagen fibers from the thus produced collagen matrix; instead, the entire collagen matrix thus produced in the present disclosure is directly subject to a granulation process to produce desired collagen particles, in which each particles is about 10-250 µm in diameter. Each of the collagen particles produced by the present method is constituted by collagen fibers in which the integrity of the collagen fibers are maintained, thus, the collagen particles of the present disclosure are suitable for use as biological scaffolds for host cells to grow thereon.

It is therefore a further aspect of the present disclosure to provide a method of treating a skin condition of a subject, in which the skin conditions are wounds, lines and/or depression on the skin. The method comprises the step of, administering a sufficient amount of the collagen particles of the present disclosure under the skin of the subject, so as to ameliorate or improve the skin condition. The present collagen particles are suitable for promoting wound healing, soothing lines and/or depression on the skin, particularly wounds that include, but are not limited to, surgical wounds (such as incisions), ulcers, and any other injury to the body in which the skin or other tissue is broken, cut, pierced, or torn; and lines and/or depression on the facial skin that include, but are not limited to, frown lines, lines around the mouth, worry lines, crows feet, smile lines, and facial scarring from acne or injury.

To provide those skilled in the art tools to use the present invention, the collagen particles of the present disclosure are assembled into kits for use in treating skin conditions described above. In one embodiment, the present invention provides a kit for use in a facial cosmetic surgery by use of the present collagen particles. In another embodiment, the present invention provides a kit for treating a wound of a subject by use of the present collagen particles.

The components included in the kits are: a container, the collagen particles produced in accordance with the procedure described in any examples of this invention, the collagen particles are characterized in that the integrity of collagen fibers are relatively intact and each particles is about 10- to 250 μm in diameter; and a legend associated with the container and indicating how to use the collagen particles of the present disclosure. The legend may be in a form of pamphlet, tape, CD, VCD or DVD.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Material and Methods
Cell Cultures
NIH-3T3 fibroblast cells were cultured in DMEM-high glucose with supplements, including 10% fetal bovine serum (FBS), 100 units/ml penicillin and 100 mg/ml streptomycin at 37° C. in a humidified atmosphere with 5% CO2.

Recellularization on the Collagen Particles
3T3 cells were grown to 80% confluent, then harvested by enzyme treatment (0.25% trypsin in 1 mM EDTA), and centrifugation at 500×g for 5 min. The collected cells were re-suspended in culture medium and seeded in the SCF-treated collagen particles at the concentration of $1\times10^3$ cells/mL, and the particles were then placed in a 24-wells culture plate and cultured for 12, 24, 48 or 72 hours in the incubator to ensure cells were attached onto the surface. The collagen particles with 3T3 cells grown thereon were then fixed by immersing in 2.5% glutaraldehyde for 1.5 hrs, and 1% oximum tetraoxide for 1.5 hrs, then dehydrated by immersing in alcohol.

Animals
New Zealand white rabbits (each weighted more than 0.5 or 2 Kg) were used in the pyrogen study and intracutaneous irritation study; Institute of Cancer Research (ICR) mice (BioLASCO Taiwan Co., Ltd., each weighted about 17-23 g) were used in skin sensitization study, and Guinea pigs (each weighted about 300-500 g) were used in the skin sensitization study. The rabbits (1 rabbit/cage), the mice (5 mice/cage), and the Guinea pigs (5 Guinea pigs/cage) were maintained in the animal facility with food and water provided ad libitum, the temperature and humidity of the animal facility were respectively kept at 18-26° C. and 30-75%. Body temperatures of the New Zealand white rabbits were recorded daily, and those with body temperatures not exceeding 39.8° C. and no more than 1° C. difference between the highest and lowest body temperatures, were selected for pyrogen study. All animals were subject to quarantine and acclimate before each test began.

Example 1

Preparation and Characterization of the Collagen Particles 1.1 Preparation of Collagen Matrix
A de-haired and de-fatted porcine rind of 0.2-0.4 mm was dried at 4° C. for 24 hrs, then was treated with scCO2 at 350 Bar, 37° C. for 40-180 min to remove any residual cellular matters.

The decellularized porcine rind was then subjected to various treatments at room temperature (about 22-28° C.), including sonicating, washing, enzymatic digestion and washing. Briefly, the decellularized porcine rind was sonicated (0.1 M Tris) for 1 hr, shaked at a speed of 100 rpm for 22 hrs, and sonicated again for another hour. Then, washed the sonicated porcine rind in sequence with, water (10 min/wash, 2 washes), a solution containing 1% Triton X-100 (shaking at a speed of 100 rpm, 24 hrs), and water (10 min each wash, total of 2 washes), so as to remove any impurities and produced a collagen matrix. The collagen matrix was then treated with a pepsin solution (0.01% pepsin in 0.5M acetic acid) for 1 hr, followed by washing with water (10 min/wash, 2 washes) while shaking at a speed of 100 rpm.

The collagen matrix was then treated with a DNAase solution (0.3 U/cm$^2$) at 37° C. for 1 hr, then washed with 1% Triton X-100 (shaking at a speed of 100 rpm for 24 hrs), and water (10 min/wash, 2 washes) at room temperature (about 22-28° C.). Then, the collagen matrix was placed in 1% H$_2$O$_2$ solution and subjected to shaking at a speed of 65 rpm for 1 hr, washed with water (10 min/wash, 2 washes) at room temperature (about 22-28° C.), and vacuum dried at 37° C. for about 8-30 min. Then, it was further treated with scCO$_2$ at 350 Bar, 37° C. for 60 min in the presence of 10% (vol %) ethanol; followed by rehydrating in water at 25° C. for 10 min, and vacuum dried at 37° C. for about 8-30 min.

1.2 Production of Collagen Particles
The rehydrated collagen matrix of example 1.1 was sliced and milled into particles using Freezer/Mill (6770/6870, 5-25 cycles). The thus produced collagen particles were irradiated with gamma ray (10-50 kGy) and stored at a sterized condition until use.

Electromicroscopy (EM) analysis indicated that each of thus produced collagen particles possessed relatively intact fibril structure (FIG. 1).

Figure 2:
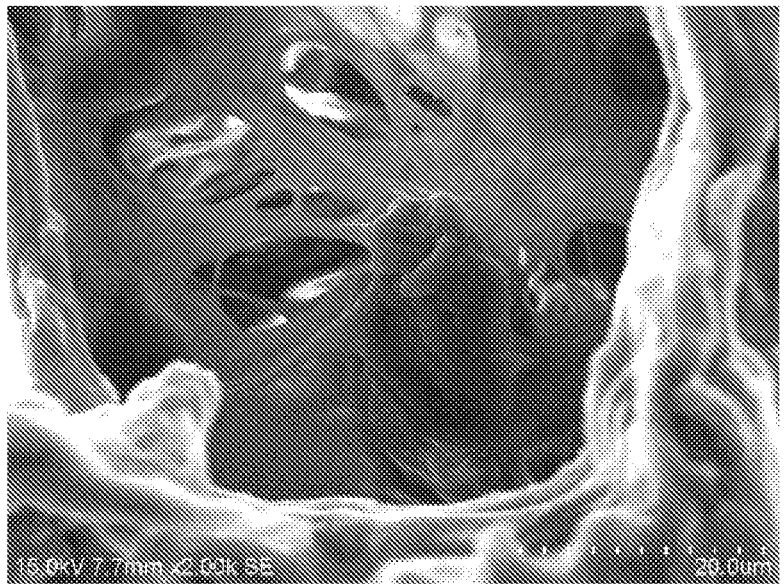
FIG. 2 are EM photographs of the present collagen particle after recellularizing 3T3 cells for (A) 12 hrs, and (B) 72 hrs in accordance with one embodiment of the present disclosure, EM photos are respectively taken at a magnification of (A) 2,000× and (B) 4,000×.
Figure 2:
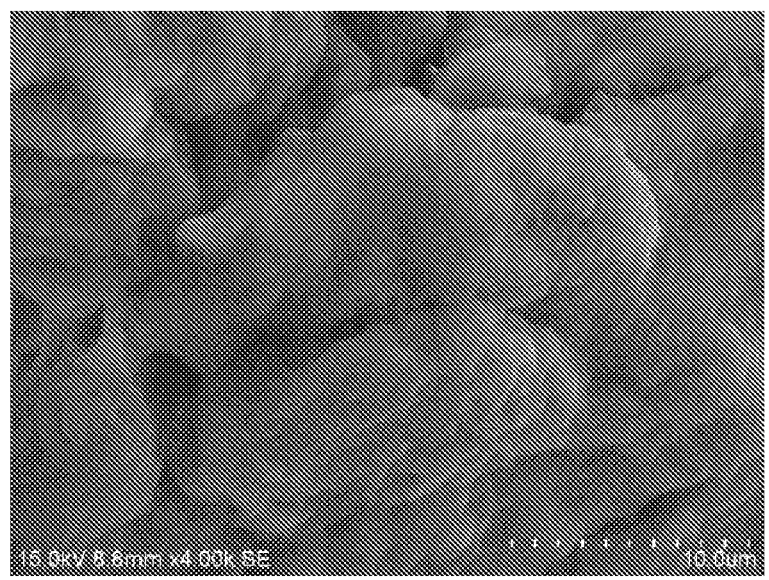

1.3 Collagen Particles of Example 1.2 Support Growth of 3T3 Cells
The collagen particles of example 1.2 was recellularized in accordance with the procedures described in the "Materials and Methods" section. The porosity of the collagen particles of example 1.2 served as an excellent biological scaffold in supporting the growth of the newly seeded 3T3 cells (FIG. 2, panel A), the entire particle was convered with 3T3 cells after being cultured for 72 hrs (FIG. 2, panel B).

Example 2

Allergy Tests the Collagen Particles of Example 1

To evaluate the potential risk of the present collagen particles in causing any allergic reaction to their hosts, a collagen extract was produced from the collagen matrix of example 1.1, then was used in various allergic tests, including pyrogen study, skin sensitization study, acute system injection study, and intracutaneous irritation study in accordance with relevant approved procedures, particularly, ISO 10993-10, 11.

2.1 Preparation of the Collagen Extract

The collagen matrix of example 1.1 (3×4 cm) was immersed in 0.9% saline or cottonseed oil at 50° C. for 72 hrs with constant agitation (150 rpm) to produce the collagen extract in saline or the collagen extract in cottonseed oil. The surface ratio of collagen matrix/0.9% saline or cottonseed oil was approximately 1 cm²/1 mL.

2.2 Pyrogen Study

The pyrogen study was conducted in accordance with the protocols set forth in U.S. Pharmacopoeia National Formulary USP36/NF31(151). Briefly, 6 male New Zealand white rabbit (>1.5 Kg, 3 rabbits in the control group and 3 rabbits in the test group) were used in this study, and 10 mL/Kg of the collagen extract in saline of example 2.1 was injected into the ear vein of each rabbits. The rabbits in the control group received just the 0.9% saline injection. The administration was completed in 10 minutes. Body temperatures of the test rabbits were respectively measured 1, 1.5, 2, 2.5 and 3 hrs after the administration of the collagen extract.

The body temperatures of the control rabbits were 39.1, 38.8 and 38.8° C., respectively (Table 1), whereas slight fluctuations in the body temperatures of the test rabbits after the administration of the collagen extract in slaine were observed; however, the fluctuations were still considered to be within the accetable range (Table 2), indicating the collagen extract derived from the collagen matrix of example 1 was pyrogen free.

TABLE 1

Body temperature of the test rabbits before the administration of the collagen extract

| Animal number | Body temperature before administration (° C.) | | Control Temperature |
|---|---|---|---|
| | 1st | 2nd | |
| # 1 | 39.1 | 39.1 | 39.1 |
| # 2 | 38.6 | 38.8 | 38.8 |
| # 3 | 38.8 | 38.8 | 38.8 |

TABLE 2

Body temperature of the test rabbits after the administration of the collagen extract

| Animal number | Body temperature (° C.) measured at designated time post administration | | | | | HBT-CT (° C.) |
|---|---|---|---|---|---|---|
| | 1 hr | 1.5 hr | 2 hrs | 2.5 hrs | 3 hrs | |
| # 1 | 39.1 | 38.8 | 38.7 | 38.7 | 38.7 | 0 |
| # 2 | 38.5 | 38.5 | 38.6 | 38.4 | 38.4 | −0.2 |
| # 3 | 39.1 | 38.9 | 38.8 | 38.6 | 38.8 | 0.3 |

HBT: the highest body temperature
CT: the control temperature of the test animals in Table 1

2.3 Skin Sensitization Study

The skin sensitization study was conducted in accordance with the protocols set forth in ISO 10993-10. Total of 30 male guinea pigs were randomly assigned to 4 groups, i.e., the control-1 (N=5), the control-2 (N=5), treatment-1 (N=10) and treatment-2 (N=10) groups. Prior to the study, the furs on the backside of the test animals were clipped from neck to scapular area with an electronic shaver, 3 clipped areas respectively designated as A, B, and C were created on the left side of each animals, and 3 clipped areas respectively designated as A, B, and C were also created on the right side in a similar manner, with each area being about 2×2 cm² in size.

On day 1 of the treatment, animals in each group received intradermal injection of 0.1 mL of the respective solutions indicated in Tables 3 or 4 for the "introduction (I) period" in the respective clipped areas. A week later, 10% sodium dodecyl sulfate (SDS) was applied to the injection areas if the animals exhibited no irritation reaction, then the same injection areas were covered with patches pre-soaked with 0.2 mL of the solution indicated for "introduction (II) period" in Table 3 or 4. Two weeks after the treatments in "introduction (II) period," the furs of the lower backside of the animals were clipped from scapular to hip area, and an appropriate site of this hairless area was selected and covered with a patch pre-soaked with 0.1 mL of the solution indicated in Tables 3 or 4 for the "Challenge period."

TABLE 3

| Test periods | Treatment Solution | | | |
|---|---|---|---|---|
| | Treatment-1 group (10 animals) | | Control-1 group (5 animals) | |
| | Area | | Area | |
| Induction (I) | A | an emulsion of 0.9% saline and FCA in 1:1 volume ratio | A | an emulsion of 0.9% saline and FCA in 1:1 volume ratio |
| | B | the collagen extract | B | 0.9% saline |
| | C | an emulsion of the collagen extract and E-FCA in 1:1 volume ratio | C | an emulsion of 0.9% saline and FCA in 1:1 volume ratio |
| Induction (II) | A, B, C | the collagen extract | A, B, C | 0.9% saline |
| Challenge | A, B, C | the collagen extract | A, B, C | 0.9% saline |

FCA: Freund's complete adjuvant

TABLE 4

| Test periods | Treatment Solution | | | |
|---|---|---|---|---|
| | Treatment-2 group (10 animals) | | Control-2 group (5 animals) | |
| | Area | | Area | |
| Induction (I) | A | an emulsion of cottonseed oil and FCA in 1:1 volume ratio | A | an emulsion of cottonseed oil and FCA in 1:1 volume ratio |
| | B | the collagen extract in cottonseed oil | B | Cottonseed oil |
| | C | an emulsion of the collagen extract and FCA in 1:1 volume ratio | C | an emulsion of cottonseed oil and FCA in 1:1 volume ratio |
| Induction (II) | A, B, C | the collagen extract in cottonseed oil | A, B, C | Cottonseed oil |
| Challenge | A, B, C | the collagen extract in cottonseed oil | A, B, C | Cottonseed oil |

The skin in the clipped area were observed 24 and 48 hrs after the challenge to see if any of the areas developed irritation and/or allergic response. The results indicated that, neither animals in the control or treatment groups exhibited any visible irritation signs on the test areas. Thus, the collagen extract of the present invention did not cause delayed hypersensitivity on the skin of the test guinea pigs.

2.4 Intracutaneous Irritation Study

This irritation study was conducted in accordance with the protocols set forth in ISO 10993-10. Briefly, 6 male New Zealand white rabbit (>2 Kg, 3 rabbits in the control group and 3 rabbits in the test group) were used in this study. Prior to the study, the furs on the backside of the test animals were clipped with an electronic shaver. On the treatment day, about 0.2 mL of the collagen extract in saline of example 2.1 was injected into 5 sites on the left side of each rabbit; and about 0.2 mL of the collagen extract in cottonseed oil of example 2.1 was injected into another 5 sites on the right side of each rabbit. The rabbits in the control group received 0.2 mL of the 0.9% saline or cottonseed oil injections at the same sites. The animals were then subject to observation at 24, 48 and 72 hrs post-administration, to see if any dermal reaction occurred at the treatment sites.

No significant clinical signs of intracutaneous irritation were found in either the control animals or treatment animals, and no mortality was found either. Thus, a single topical application of the collagen extract did not cause intracutaneous irritation in New Zealand White Rabbits.

2.5 Acute System Injection Study

This acute system injection study was conducted in accordance with the protocols set forth in ISO 10993-11. Total of 20 male guinea pigs were randomly assigned to 4 groups, i.e., the control-1 (N=5), the control-2 (N=5), treatment-1 (N=5) and treatment-2 (N=5) groups.

On day 1 of the treatment, animals in the treatment-1 group received a single dose intravenous injection of the collagen extract in saline (50 mL/Kg), whereas animals in the treatment-2 group received a single dose intraperitoneal injection of the collagen extract in cottonseed oil (50 mL/Kg). The animals in control-1 and control-2 received injections of 0.9% saline and cottonseed oil, respectively. Mice were then subject to toxicity observation respectively at 4, 24, 48 and 72 hrs post-administration.

No significant clinical signs of toxicity were found in either the control animals or treatment animals, and no mortality was found either. Thus, a single application of the collagen extract did not cause toxicity reaction in the test animals.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method for preparing a collagen particle comprising:
   (1) subjecting an animal skin having a thickness of about 0.1-1 mm to a treatment of a supercritical fluid (SCF) under a pressure of 100-500 bar at a temperature between 30-50° C. for 20 min to 5 days;
   (2) subjecting the SCF treated animal skin of step (1) to the treatment of an aqueous solution comprising a non-ionic surfactant selected from the group consisting of octylphenol ethoxylates, sorbitan monostearate, polysorbate, poloxomer, nonoxynols, cetyl alcohol, and alkylpolyglucoside;
   (3) subjecting the aqueous solution treated animal skin of the step (2) to the treatment of a protease, which is selected from the group consisting of pepsin, trypsin, chymotrypsin, papain, chymopapain, bromelain, actinidain, proteinase A, proteinase K, peptidase, ficin, calpain, caspase, and a combination thereof;
   (4) subjecting the protease treated animal skin of step (3) to the treatment of a nuclease, which is a DNA nuclease or a RNA nuclease;
   (5) subjecting the nuclease treated animal skin of step (4) to the treatment of a hydrogen peroxide solution for an hour;
   (6) subjecting the hydrogen peroxide treated animal skin of step (5) to a chemical removal process so as to produce a collagen matrix from the treated animal skin; and
   (7) subjecting the collagen matrix of step (6) to a granulation process so as to produce the collagen particle having a size of 10-250 μm.

2. The method of claim 1, wherein the SCF is any of a supercritical carbon dioxide ($scCO_2$), a supercritical nitrous oxide ($scN_2O$), a supercritical water ($scH_2O$), a supercritical alkane, a supercritical alkene, a supercritical alcohol or a supercritical acetone.

3. The method of claim 2, wherein the SCF is $scCO_2$ or $scN_2O$.

4. The method of claim 2, wherein in the SCF treatment, the temperature is 37° C., and the pressure is 350 Bar.

5. The method of claim 1, wherein the aqueous solution of step (2) further comprises a salt or an anionic surfactant selected from the group consisting of lauryl sulfonic acid, dodecyl sulfonic acid, sodium dodecyl sulfate (SDS), dodecyl benzene sulfonic acid, tridecyl benzene sulfonic acid, alkyl-phenoxy benzene disulfonic acid, naphthalene sulfonic acid, alkyl-naphthalene sulfonic acid, and alkenyl-naphthalene.

6. The method of claim 1, wherein the nuclease treated animal skin of step (4) is further treated with the aqueous solution of the step (2).

7. The method of claim 1, wherein in the step (6), the hydrogen peroxide treated animal skin of step (5) is subject to the treatment of the SCF under a pressure of 100-500 bar at a temperature between 30-50° C. for 20 min to 5 days.

8. The method of claim 7, wherein the SCF is selected from the group consisting of a supercritical carbon dioxide ($scCO_2$), a supercritical nitrous oxide ($scN_2O$), a supercritical water ($scH_2O$), a supercritical alkane, a supercritical alkene, a supercritical alcohol and a supercritical acetone.

9. The method of claim 8, wherein the SCF is $scCO_2$ or $scN_2O$.

10. The method of claim 7, wherein the SCF is applied to the hydrogen peroxide treated animal skin of step (5) along with a co-solvent.

11. The method of claim 10, wherein the col-solvent is ethanol.

12. The method of claim 7, wherein in the SCF treatment the temperature is 37° C., and the pressure is 350 Bar.

13. The method of claim 1, wherein the granulation process of step (7) is performed by cutting or grinding the collagen matrix of step (6) in the presence of liquid nitrogen so as to produce the collagen particle having a size of 10-250 μm.

* * * * *